(12) United States Patent
Brinkmann et al.

(10) Patent No.: US 8,673,982 B2
(45) Date of Patent: Mar. 18, 2014

(54) CERAMIDE-ANALOGOUS METABOLITES

(75) Inventors: Volker Brinkmann, Freiburg (DE); Guido Jordine, Freiburg (DE); Markus Zollinger, Möhlin (CH); Claudia Sayer, Bad Krozingen (DE)

(73) Assignee: Novartis AG, Basel (CH)

( * ) Notice: Subject to any disclaimer, the term of this patent is extended or adjusted under 35 U.S.C. 154(b) by 309 days.

(21) Appl. No.: 13/202,939

(22) PCT Filed: Feb. 23, 2010

(86) PCT No.: PCT/EP2010/052231
§ 371 (c)(1),
(2), (4) Date: Aug. 23, 2011

(87) PCT Pub. No.: WO2010/097371
PCT Pub. Date: Sep. 2, 2010

(65) Prior Publication Data
US 2011/0306672 A1    Dec. 15, 2011

(30) Foreign Application Priority Data

Feb. 24, 2009   (EP) .................................. 09153550

(51) Int. Cl.
*A01N 37/18* (2006.01)
*C07C 211/03* (2006.01)
*C07C 233/08* (2006.01)
*C07C 235/00* (2006.01)

(52) U.S. Cl.
USPC ........... 514/630; 514/613; 514/625; 514/579; 514/627; 564/336; 564/342; 564/383; 564/223; 564/123; 554/35; 554/66; 554/69; 554/103

(58) Field of Classification Search
None
See application file for complete search history.

(56) References Cited

U.S. PATENT DOCUMENTS

| | | | | |
|---|---|---|---|---|
| 5,604,229 A | * | 2/1997 | Fujita et al. | 514/252.1 |
| 5,719,176 A | * | 2/1998 | Fujita et al. | 514/440 |
| 5,948,820 A | * | 9/1999 | Fujita et al. | 514/653 |
| 5,952,316 A | * | 9/1999 | Fujita et al. | 514/114 |
| 6,187,821 B1 | * | 2/2001 | Fujita et al. | 514/653 |

FOREIGN PATENT DOCUMENTS

| | | |
|---|---|---|
| EP | 0627406 A | 12/1994 |
| EP | 0778263 A | 6/1997 |

OTHER PUBLICATIONS

Kiuchi, M. et al., Syunthesis and immunosuppressive activity of 2-substituted 2-aminopropane-1,3-diols and 2-aminoethanols, 2000, J. Med. Chem., vol. 43, No. 15, pp. 2946-2961.*
Gao et al, Research Progresses of a New Immunosuppressor FTY720, World Notes on Antibiotics, vol. 28, No. 5, pp. 215-218, 2007.
Chemical Structural Modification of Drugs, Chapter 17, Pharmacy II, Guidelines for National Pharmacist Qualification Examination, edited by Pharmacist Qualification Center of SFDA, p. 565, Chinese Traditional Medicine Publishing House, Apr. 2003.
Kappas Ludwig et al.; Oral Fingolimod (FTY720) for relapsing muzltiple sclerosis, Journal of Medizin vol. 355, No. 11, 2006.
D.J. Buzard et al.; Recent progress in the development., Expert Opinion on Therap.Patents, vol. 18, No. 10 pp. 1141-1159, 2008.
M. Kiuchi et.al., Journal of .Med.Chemisty vol. 43, pp. 2946-2961, 2000.

* cited by examiner

*Primary Examiner* — Yate K Cutliff
(74) *Attorney, Agent, or Firm* — Andrew Holmes

(57) ABSTRACT

This invention relates to certain ceramide-analogues of FTY720 (2-amino-2-[2-(4-octylphenyl)ethyl]propane-1,3-diol; fingolimod). In particular, the present invention relates to pharmaceutical compositions comprising these compounds, as well as processes for their preparation and their use in the treatment of autoimmune conditions, such as multiple sclerosis.

5 Claims, No Drawings

CERAMIDE-ANALOGOUS METABOLITES

This application is a National Stage of International Application No. PCT/EP2010/052231 filed on Feb. 23, 2010, which claims benefit of European Application No. 09153550.0 filed on Feb. 24, 2009, the entire disclosures of which are hereby incorporated by reference.

FIELD OF THE INVENTION

This invention relates to certain ceramide-analogues of FTY720 (2-amino-2-[2-(4-octylphenyl)ethyl]propane-1,3-diol; fingolimod). In particular, the present invention relates to pharmaceutical compositions comprising these compounds, as well as processes for their preparation and their use in the treatment of autoimmune conditions, such as multiple sclerosis.

BACKGROUND OF THE INVENTION

European Patent Publication Number 627,406 (A1), the relevant disclosure of which is incorporated herein by reference, discloses a series of 2-amino-2-[2-(4-$C_{2-20}$-alkyl-phenyl)ethyl]propane-1,3-diol compounds. On the basis of observed activity, the compounds have been found to be useful as immunosuppressants. Accordingly, the compounds may be useful in the treatment or prevention of various autoimmune conditions, including multiple sclerosis. A particular compound in this class is FTY720 (2-amino-2-[2-(4-octylphenyl)ethyl]propane-1,3-diol; fingolimod), which may be obtained in the form of the free base or as a hydrochloride salt. The structure of FTY720 is shown below:

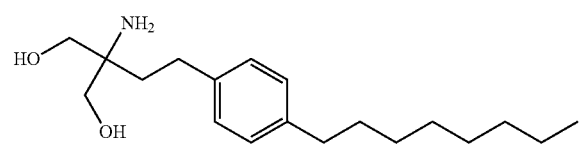 [SMILES: CCCCCCCCc1ccc(CCC(N)(CO)CO)cc1]

FTY720 is known to be metabolised in vivo by three pathways. The three pathways concerned are: (i) reversible phosphorylation to FTY720-phosphate (FTY720-P), (ii) oxidation at the terminal methyl group of the octyl chain to yield the octanoic acid derivative, followed by successive loss of two carbon units though β-oxidation to give the hexanoic acid, butyric acid and acetic acid derivatives, and (iii) formation of non-polar ceramide derivatives (Zollinger et al. Abstracts from the 10th European Regional ISSX Meeting, Drug Metabolism Reviews, 2008, 40:S1, page 125).

Certain ceramide analogues of FTY720 have now been identified and characterised. These ceramide analogues are potential new agents for treatment of autoimmune diseases, such as multiple sclerosis.

DISCLOSURE OF THE INVENTION

Thus, the present invention relates to the following Compounds I to IV, which are ceramide analogues of FTY720 formed by the metabolism of FTY720 in animals and man:

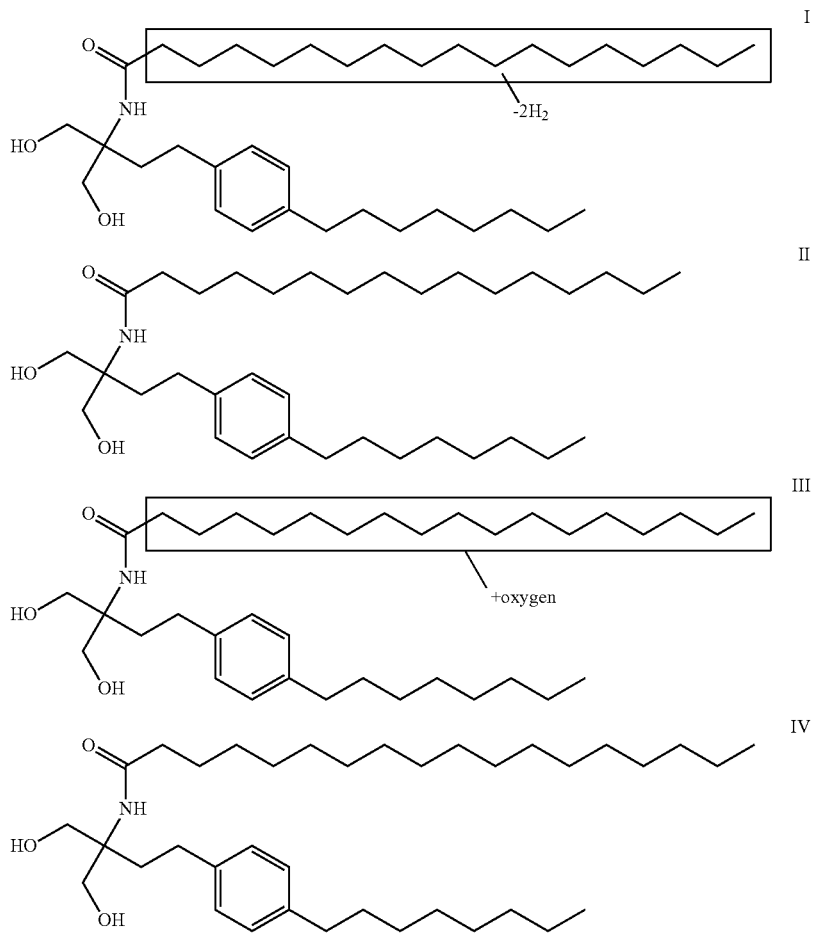

In Compound I above, the box around the alkyl chain of the fatty acid component is labelled "$-2H_2$" to indicate that two double bonds are located along the length of the alkyl chain, i.e. it is the acylation product of FTY720 and an octadecadienoic acid (such as linoleic acid).

In Compound III above, the box around the alkyl chain of the fatty acid component is labelled "+oxygen" to indicate that somewhere along the length of the alkyl chain there is a hydroxyl group, i.e. it is the product of acylating FTY720 with a hydroxyoctadecanoic acid.

Compounds II and IV are the products of acylating FTY720 with palmitic acid and stearic acid respectively.

Therefore, in a first aspect, the present invention relates to an isolated form of any one of Compounds I to IV above.

By "isolated form" we mean that the compound is free from any of the components that would normally accompany it when it is formed metabolically in vivo. For example, it is free of any biological matter, such as serum components, as well as other metabolites of FTY720 formed in vivo. Suitably, the compound is in a purified and isolated form. By "purified" we mean that the compound is conveniently greater that 75% pure, more conveniently greater than 90% pure, and preferably greater than 95% pure and most preferably greater than 98% pure.

Pharmaceutical Preparations

In another aspect, the present invention provides a pharmaceutical composition comprising any one of the Compounds I to IV above in association with a pharmaceutically acceptable adjuvant, diluent or carrier. In one embodiment there is provided a pharmaceutical composition comprising the Compound I, or the Compound II, or the Compound III or the Compound IV, in association with a pharmaceutically acceptable adjuvant, diluent or carrier.

A pharmaceutical composition according to the invention may be administered orally, intravenously, subcutaneously, buccally, rectally, dermally, nasally, tracheally, bronchially, by any other parenteral route, or via inhalation.

Typically, therefore, the pharmaceutical composition of the invention may be administered orally or parenterally ("parenterally" as used herein, refers to modes of administration which include intravenous, intramuscular, intraperitoneal, intrasternal, subcutaneous and intraarticular injection and infusion) to a host.

Compounds I to IV above may be further processed before formulation into a suitable pharmaceutical formulation, for example they may be milled or ground into smaller particles.

The amount of Compound I, II, III or IV, which is employed in a pharmaceutical composition of the invention will depend on the condition, and patient, to be treated, but this can be determined non-inventively.

Pharmaceutical compositions of this invention for parenteral injection suitably comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from the site of a subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the compound is typically mixed with at least one inert, pharmaceutically acceptable excipient or carrier, such as sodium citrate or dicalcium phosphate, and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

Compound I, II, III or IV may also be in micro-encapsulated form, if appropriate, with one or more of the above-mentioned excipients.

Compound I, II, III or IV may also be in finely divided form, for example it may be micronised.

Liquid dosage forms for oral administration include pharmaceutically acceptable emulsions, solutions, suspensions, syrups and elixirs. In addition to the compound, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofuryl alcohol, polyethylene glycols and fatty acid esters of sorbitan and mixtures thereof. Besides inert diluents, the oral compositions may also include adjuvants such as wetting agents, emulsifying and suspending agents, sweetening, flavouring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal administration are preferably suppositories which can be prepared by mixing compound with suitable non-irritating excipients or carriers such as cocoa butter, polyethylene glycol or a suppository wax which are solid at room temperature but liquid at body temperature and therefore melt in the rectum or vaginal cavity and release the active compound.

Compound I, II, III, or IV may also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form may contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

The actual dosage levels of Compound I, II, III or IV in the pharmaceutical compositions of this invention may be varied so as to obtain an amount of the active drug that is effective to achieve the desired therapeutic response for a particular patient, compositions, and mode of administration. The selected dosage level will depend upon the activity of the compound, the route of administration, the severity of the condition being treated and the condition and prior medical history of the patient being treated. However, it is within the skill of the art to start doses of the compound at levels lower than required in order to achieve the desired therapeutic effect and to gradually increase the dosage until the desired effect is achieved.

Process of Preparation

As previously stated, Compounds I to IV above are metabolites of FTY720 produced in vivo.

The compounds may also be prepared synthetically by acylating FTY720 with the appropriate fatty acid. Any suitable means for carrying out the acylation reaction may be used.

In a particular aspect, the present invention provides a process for preparing Compound I

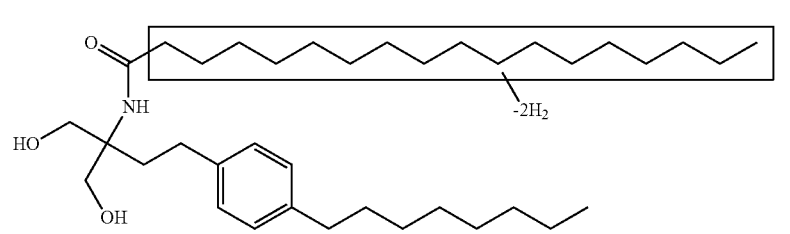

comprising the step of reacting FTY720, or a salt thereof (such as the HCl salt),

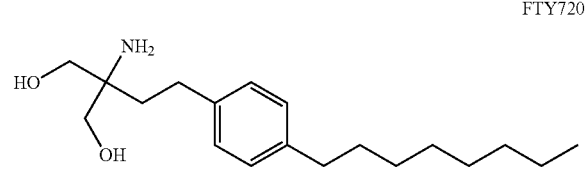 [SMILES: CCCCCCCCc1ccc(CCC(N)(CO)CO)cc1]

with a compound of the general formula A:

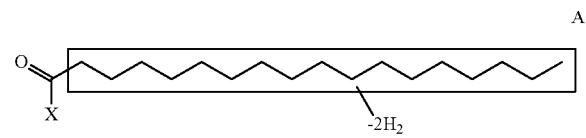

where X is a suitable leaving group;
in the presence of a suitable solvent.

In a further aspect, the present invention provides a process for preparing Compound II

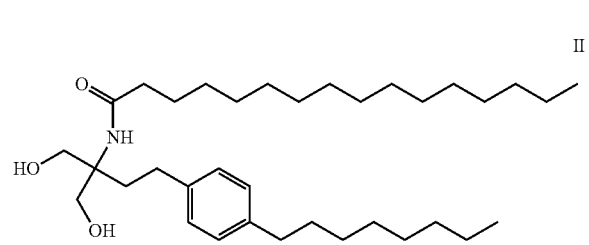 [SMILES: CCCCCCCCCCCCCCCC(=O)NC(CO)(CO)CCc1ccc(CCCCCCCC)cc1]

comprising the step of reacting FTY720, or a salt thereof (such as the HCl salt),

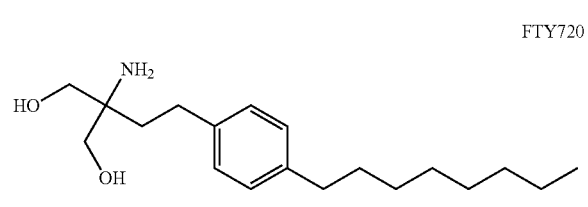 [SMILES: CCCCCCCCc1ccc(CCC(N)(CO)CO)cc1]

with a compound of the general formula B:

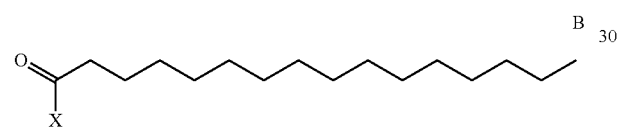

wherein X is a suitable leaving group;
in the presence of a suitable solvent.

In a further aspect, the present invention provides a process for preparing Compound III

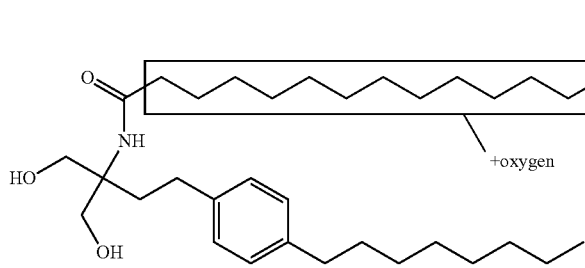

comprising the step of reacting FTY720, or a salt thereof (such as the HCl salt),

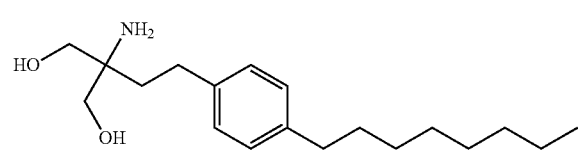

with a compound of general formula C:

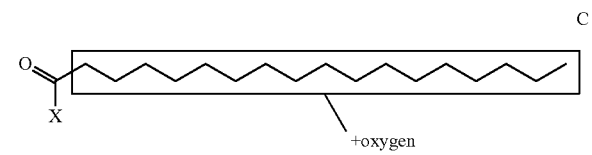

wherein X is a suitable leaving group;
in the presence of a suitable solvent.

In a further aspect, the present invention provides a process for preparing Compound IV

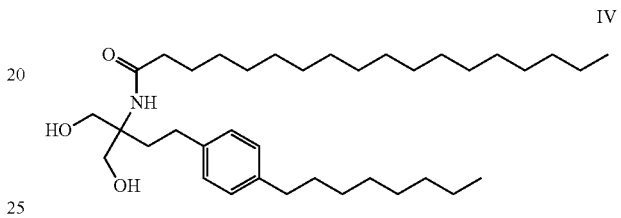

comprising the step of reacting FTY720, or a salt thereof (such as the HCl salt),

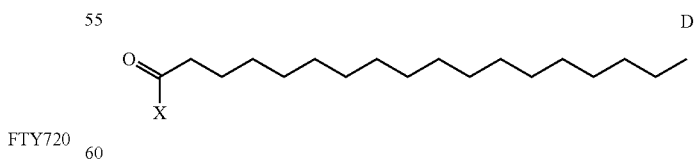

with a compound of general formula D:

D wherein X is a suitable leaving group;
in the presence of a suitable solvent.

The leaving group X may be any suitable leaving group. Suitably, X is halo and, most suitably, X is chloro.

Suitably the reaction is also carried out in the presence of a suitable base, such as triethylamine.

Any suitable solvent or mixture of solvents may be used for the acylation reactions. An example of a suitable solvent is dichloromethane.

A person skilled in the art will be able to select appropriate reaction times and conditions for carrying out the acylation reactions.

Further experimental details are provided in the Examples.

Medical Uses

Compounds I, II, III or IV may be useful in:

a) the treatment and/or prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells; and b) the treatment and/or prevention of autoimmune disease or of inflammatory conditions, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis.

In particular, Compounds I, II, III or IV, preferably Compounds I, II, or III, are potentially useful for the treatment of multiple sclerosis.

For the above uses the required dosage will of course vary depending on the mode of administration, the particular condition to be treated and the effect desired. In general, satisfactory results are indicated to be obtained at daily dosages of from about 0.1 to about 100 mg/kg body weight. An indicated daily dosage in the larger mammal, e.g. humans, is in the range of from about 0.5 mg to 2000 mg, conveniently administered, for example, in divided doses up to four times a day or in retard form.

Compounds I, II, III or IV, preferably Compounds I, II, or III, may be administered by any appropriate route, e.g. orally, for example in the form of a tablet or capsule, topically or parenterally, for example intravenously. Pharmaceutical compositions comprising these compounds in association with at least one pharmaceutically acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Compounds I, II, III or IV, preferably Compounds I, II, or III, may be administered as the sole active ingredient or together with other drugs in immunomodulating regimens or other anti-inflammatory agents e.g. for the treatment or prevention of allograft acute or chronic rejection or inflammatory or autoimmune disorders. For example, they may be used in combination with calcineurin inhibitors, e.g. cyclosporin A, cyclosporin G, FK-506, ABT-281, ASM 981; an mTOR inhibitor, e.g. rapamycin, 40-O-(2-hydroxy)ethyl-rapamycin, CCI779, ABT578 or AP23573 etc.; corticosteroids; cyclophosphamide; azathioprene; methotrexate; another S1P receptor agonist, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists.

Where one of Compounds I to IV is administered in conjunction with another immunomodulating or anti-inflammatory agent, dosages of the co-administered immunomodulating or anti-inflammatory agent will of course vary depending on the type of co-drug employed, on the condition to be treated and so forth.

In another embodiment of the invention, Compounds I, II, III or IV, e.g. Compounds I, II, or III, may be converted in vivo into FTY720. Therefore Compounds I, II, III or IV, e.g. Compounds I, II, or III, may be used to administer FTY720, e.g. for the treatment or prevention of allograft acute or chronic rejection or inflammatory or autoimmune disorders, as mentioned hereinabove.

Thus, in additional aspects, the present invention provides:

1. A method of treating or preventing organ or tissue transplant rejection, comprising administering to a subject a therapeutically effective amount of any one of Compounds I, II, III, or IV, or combination thereof, preferably any one of Compounds I, II, or III, or combination thereof.

1.1 A method of treating or preventing organ or tissue transplant rejection, comprising administering to a subject a therapeutically effective amount of a pharmaceutical composition comprising any one of Compounds I, II, III, or IV, or combination thereof, preferably any one of Compounds I, II, or III, or combination thereof, in association with a pharmaceutically acceptable adjuvant, diluent or carrier.

2. A method of treating or preventing an autoimmune disease or an inflammatory condition, comprising administering to a subject a therapeutically effective amount of any one of Compounds I, II, III, or IV, or combination thereof, preferably any one of Compounds I, II, or III, or combination thereof.

2.1 A method of treating or preventing an autoimmune disease or an inflammatory condition, comprising administering to a subject a therapeutically effective amount of a pharmaceutical composition comprising any one of Compound I, II, III, or IV, or a combination thereof, preferably any one of Compounds I, II, or III, or combination thereof, in association with a pharmaceutically acceptable adjuvant, diluent or carrier.

3. A method of treating multiple sclerosis comprising administering to a subject a therapeutically effective amount of any one of Compounds I, II, III, or IV, or combination thereof, preferably any one of Compounds I, II, or III, or combination thereof.

3.1 A method of treating multiple sclerosis comprising administering to a subject a therapeutically effective amount of a pharmaceutical composition comprising any one of Compounds I, II, III, or IV, or a combination thereof, preferably any one of Compounds I, II, or III, or combination thereof, in association with a pharmaceutically acceptable adjuvant, diluent or carrier.

4. Compound I, II, III or IV, or combination thereof, preferably any one of Compounds I, II, or III, or combination thereof, for use as a pharmaceutical.

5. A pharmaceutical composition for use in the treatment or prevention of any one of the conditions listed above, or in any one of the methods defined in paragraphs 1., 1.1, 2., 2.1, 3. or 3.1 above, comprising any one of Compounds I, II, III, or IV, or a combination thereof, preferably any one of Compounds I, II, or III, or combination thereof, and a pharmaceutically acceptable diluent or carrier.

6. Use of any one Compounds I, II, III or IV, or a combination thereof, preferably any one of Compounds I, II, or III, or combination thereof, for the preparation of a medicament for the treatment of any one of the conditions listed out hereinbefore, or in the methods set out at paragraphs 1, 1.1, 2., 2.1, 3. or 3.1 above.

7. A pharmaceutical combination comprising (a) any one of Compounds I, II, III, or IV and (b) a second drug substance, said second drug substance being suitable for the prevention or treatment of a condition described above.

8. A method as defined above comprising co-administration, e.g. concomitantly or in sequence, of (a) Compound I, II, III or IV and (b) a second drug substance, said second drug substance being suitable for the prevention or treatment of a condition described above.

9. A method of administering FTY720 to a patient in need thereof, for example a patient affected by multiple sclerosis, comprising administering any one of Compounds I, II, III, or IV, or combination thereof, or a pharmaceutical composition comprising any one of Compounds I, II, III, or IV, or a combination thereof, and a pharmaceutically acceptable diluent or carrier.

9.1. A method of administering FTY720 for the treatment of any one of the conditions listed out hereinbefore, or in the methods set out at paragraphs 1, 2, or 3 above, comprising administering to a subject a therapeutically effective amount of any one of Compounds I, II, III, or IV, or combination thereof, or a pharmaceutical composition comprising any one of Compounds I, II, III, or IV, or a combination thereof, and a pharmaceutically acceptable diluent or carrier.

9.2 A method of administering FTY720 for the treatment of multiple sclerosis comprising administering to a subject a therapeutically effective amount of any one of Compounds I, II, III, or IV, or combination thereof, or combination thereof, or a pharmaceutical composition comprising any one of Compounds I, II, III, or IV, or a combination thereof, and a pharmaceutically acceptable diluent or carrier.

10. Use of any one of Compounds I, II, III, or IV, or combination thereof as a prodrug for FTY720.

10.1 Use of any one of Compounds I, II, III, or IV, or combination thereof, or a pharmaceutical composition comprising any one of Compounds I, II, III, or IV, or a combination thereof, and a pharmaceutically acceptable diluent or carrier, for administering FTY720 to a patient in need thereof, for example a patient affected by multiple sclerosis.

EXAMPLES

The invention is illustrated, but in no way limited, by the following Examples.

Example 1

Preparation of Compound II (Palmitoyl-FTY720)

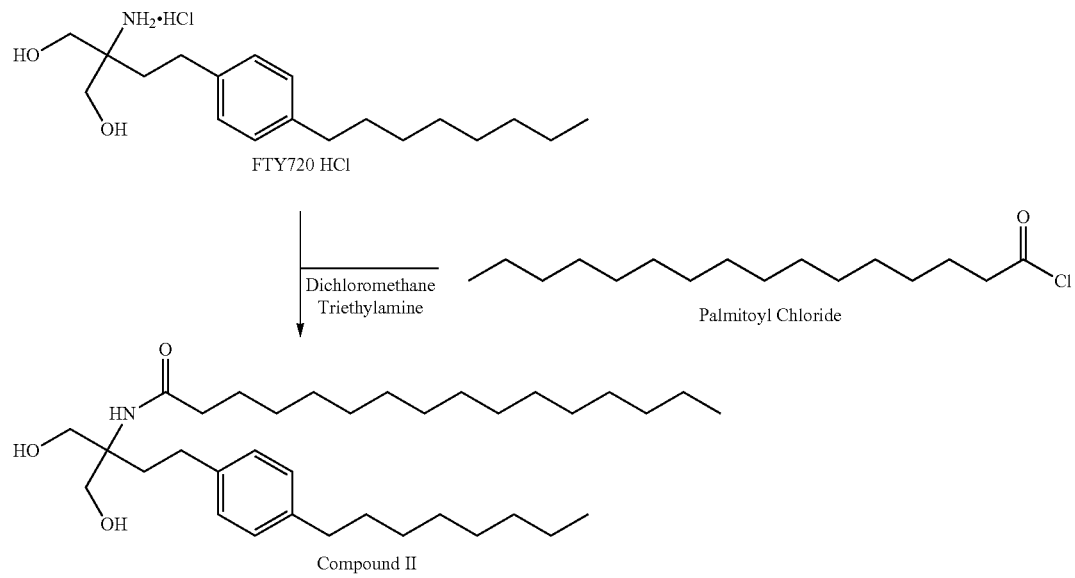

FTY720-hydrochloride (10.0 g (29.1 mmol)) is suspended in 102 ml of dichloromethane. The temperature of the solution is 22° C. Triethylamine (5.94 g (58.7 mmol)) is added over a 10 minute period at a temperature of 20-25° C. The solution is stirred for 15 minutes at 20-25° C. Palmitoylchloride (8.16 g (29.7 mmol)) is then added within a 30 minute period. The reaction is slightly exothermic, so ice is used to cool the reaction vessel and keep the temperature at 20-25° C. The solution is stirred for 2 hours at 20-25° C. A 25% by weight solution of NaCl in water (102 mL) is then added at 20-25° C. within a 15 minute period, followed by the addition of 5.3 mL of a 10% (by weight) solution of HCl in water. The phases are separated, the organic phase is washed consecutively with 75 mL of a 25% NaCl solution (in water), 75 ml of a 5% (by weight) solution of $NaHCO_3$ (in water), and three times with 75 ml water. The organic phase is then evaporated at 50° C. The product is analysed by HPLC (HPLC-analysis 97.8% b.a.)

Example 2

Preparation of Compound IV (Stearoyl-FTY720)

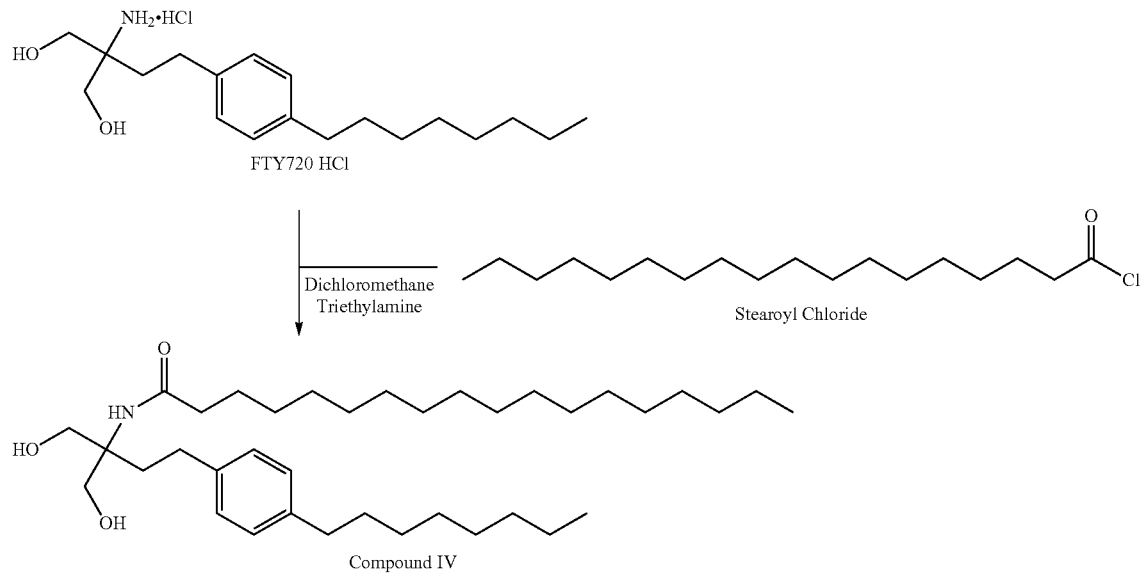

FTY720-hydrochloride (10.0 g (29.1 mmol)) is suspended in 81.4 mL of dichloromethane. The temperature of the solution is 22° C. Triethylamine (5.94 g (58.7 mmol)) is added within a 10 minute period at a temperature of 20-25° C. The solution is then stirred for 15 minutes at 20-25° C. Stearoyl-chloride (9.03 g (29.8 mmol)) is then dissolved in 15.3 mL of dichloromethane and added to the FTY720-hydrochloride solution within a 30 minute period.

The reaction is slightly exothermic and requires cooling by ice to keep the temperature at 20-25° C. Stirring continued for 2 hours at 20-25° C. followed by the addition of 102 mL of a 25% (by weight) solution of NaCl in water at 20-25° C. within a 15 minute period, then the addition of 5.3 mL of a 10% (by weight) HCl solution (in water). The phases are then separated and the organic phase is subjected to consecutive washes with 75 mL of a 25% NaCl-solution (in water), 75 mL of a 5% (by weight) solution of $NaHCO_3$ (in water), and three washes with 75 mL of water. The organic phase is then evaporated at 50° C. The product is analysed by HPLC (HPLC-analysis 98.0% b.a.).

The invention claimed is:

1. A pharmaceutical composition comprising a compound of formula I, II, III or IV, or a combination thereof

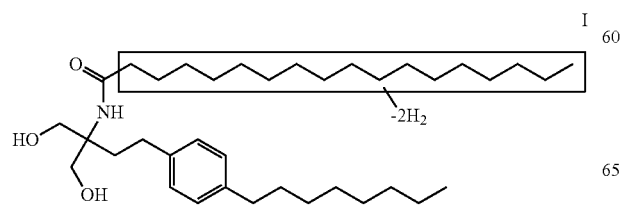

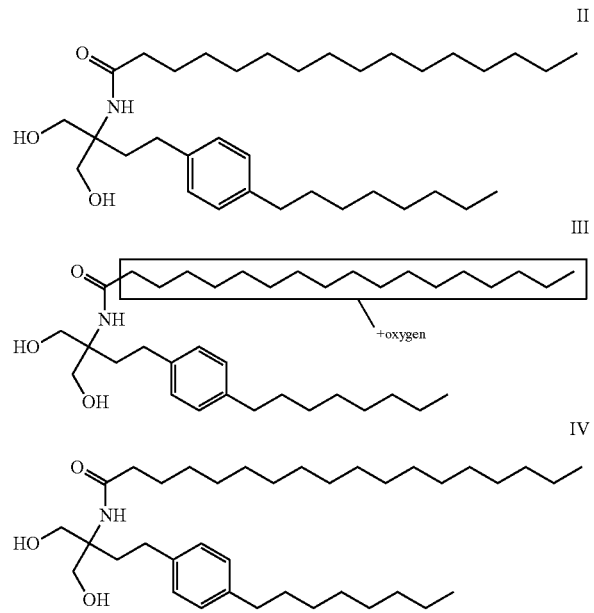

wherein in Compound I, the box labelled -$2H_2$ surrounding the alkyl chain means that there are two carbon-carbon double bonds positioned along the length of the alkyl chain, and in Compound III, the box labelled +oxygen surrounding the alkyl chain means that there is a hydroxyl group positioned along the length of the alkyl chain;

in admixture with a pharmaceutically acceptable adjuvant, diluent or carrier.

2. A pharmaceutical composition according to claim 1, wherein the composition comprises Compound I.

3. A pharmaceutical composition according to claim 1, wherein the composition comprises Compound II.

4. A pharmaceutical composition according to claim 1, wherein the composition comprises Compound III.

5. A pharmaceutical composition according to claim 1, wherein the composition comprises Compound IV.

* * * * *